US007909831B2

(12) United States Patent
Axelson, Jr. et al.

(10) Patent No.: US 7,909,831 B2
(45) Date of Patent: *Mar. 22, 2011

(54) SYSTEMS USED IN PERFORMING FEMORAL AND TIBIAL RESECTION IN KNEE SURGERY (75) Inventors: Stuart L. Axelson, Jr., Succasunna, NJ (US); Jose Luis Moctezuma, Freiburg (DE); Kenneth A. Krackow, Williamsville, NY (US); Mattthew P. Poggie, Upper Montclair, NJ (US); Gearoid Walsh, Ennis (IE)

(73) Assignee: Howmedica Osteonics Corp., Mahwah, NJ (US)

( * ) Notice: Subject to any disclaimer, the term of this patent is extended or adjusted under 35 U.S.C. 154(b) by 535 days.

This patent is subject to a terminal disclaimer.

(21) Appl. No.: 09/811,042

(22) Filed: Mar. 17, 2001

(65) Prior Publication Data
US 2002/0133160 A1 Sep. 19, 2002

Related U.S. Application Data (60) Provisional application No. 60/272,641, filed on Feb. 28, 2001.

(51) Int. Cl.
*A61F 5/00* (2006.01)
(52) U.S. Cl. ........................................................ 606/87
(58) Field of Classification Search .................. 606/53, 606/130, 1, 80–89, 96
See application file for complete search history.

(56) References Cited

U.S. PATENT DOCUMENTS

| 4,474,177 | A | | 10/1984 | Whiteside |
| 4,487,203 | A | | 12/1984 | Androphy |
| 4,502,483 | A | | 3/1985 | Lacey |
| 4,524,766 | A | | 6/1985 | Petersen |
| 4,567,885 | A | | 2/1986 | Androphy |
| 4,653,488 | A | | 3/1987 | Kenna et al. |
| 4,718,413 | A | | 1/1988 | Johnson |
| 4,892,093 | A | | 1/1990 | Zarnowski et al. |
| 4,952,213 | A | | 8/1990 | Bowman et al. |
| 4,979,949 | A | * | 12/1990 | Matsen et al. .................. 606/53 |
| 5,002,547 | A | | 3/1991 | Poggie et al. |
| 5,053,037 | A | | 10/1991 | Lackey |
| 5,342,368 | A | | 8/1994 | Petersen |
| 5,364,401 | A | | 11/1994 | Ferrante et al. |
| 5,417,695 | A | | 5/1995 | Axelson, Jr. |
| 5,454,816 | A | | 10/1995 | Ashby |
| 5,474,559 | A | | 12/1995 | Bertin et al. |
| 5,601,563 | A | | 2/1997 | Burke et al. |

(Continued)

FOREIGN PATENT DOCUMENTS

FR 2703584 4/1993

(Continued)

OTHER PUBLICATIONS

European Search Report re: 04250551.1-1265 dated May 14, 2004.

*Primary Examiner* — Anu Ramana
(74) *Attorney, Agent, or Firm* — Lerner, David, Littenberg, Krumholz & Mentlik, LLP (57) ABSTRACT A system for resecting a tibia and femur during arthroplasty includes anchoring devices, a three-way alignnment guide attachable to an anchoring device. The alignment guide provides for locating a resection guide in three degrees of freedom, including one translation and two rotations. The resection guide is coupled to a computer navigation system.

27 Claims, 8 Drawing Sheets

U.S. PATENT DOCUMENTS

| | | | |
|---|---|---|---|
| 5,624,444 A | 4/1997 | Wixon et al. | |
| 5,630,431 A * | 5/1997 | Taylor | 128/897 |
| 5,653,714 A | 8/1997 | Dietz et al. | |
| 5,658,292 A | 8/1997 | Axelson, Jr. | |
| 5,681,316 A | 10/1997 | DeOrio et al. | |
| 5,690,635 A * | 11/1997 | Matsen, III et al. | 606/88 |
| 5,704,941 A * | 1/1998 | Jacober et al. | 606/88 |
| 5,743,915 A | 4/1998 | Bertin et al. | |
| 5,749,876 A | 5/1998 | Duvillier et al. | |
| 5,788,700 A * | 8/1998 | Morawa et al. | 606/88 |
| 5,830,216 A | 11/1998 | Insall et al. | |
| 6,077,270 A | 6/2000 | Katz | |
| 6,090,114 A | 7/2000 | Matsuno et al. | |
| 6,267,762 B1 * | 7/2001 | Millard et al. | 606/54 |
| 6,285,902 B1 * | 9/2001 | Kienzle et al. | 600/427 |
| 6,348,058 B1 | 2/2002 | Melkent et al. | |
| 6,385,475 B1 | 5/2002 | Cinquin et al. | |
| 6,450,978 B1 * | 9/2002 | Brosseau et al. | 600/595 |
| 6,514,259 B2 | 2/2003 | Picard | |
| 6,533,737 B1 * | 3/2003 | Brosseau et al. | 600/595 |
| 6,554,837 B1 * | 4/2003 | Hauri et al. | 606/87 |
| 6,685,711 B2 * | 2/2004 | Axelson et al. | 606/88 |
| 6,711,432 B1 * | 3/2004 | Krause et al. | 600/427 |
| 6,859,661 B2 * | 2/2005 | Tuke | 600/424 |
| 2001/0001121 A1 | 5/2001 | Lombardo et al. | |
| 2002/0147455 A1* | 10/2002 | Carson | 606/130 |

FOREIGN PATENT DOCUMENTS

| | | | |
|---|---|---|---|
| FR | 2776176 | | 9/1999 |
| WO | WO0000093 | * | 1/2000 |

* cited by examiner

SYSTEMS USED IN PERFORMING FEMORAL AND TIBIAL RESECTION IN KNEE SURGERY

PRIOR PROVISIONAL APPLICATION

This application relates to and claims priority from a provisional application Ser. No. 60/272,641 entitled "Methods, Systems and Tools Used In Performing Femoral and Tibial Resection In Knee Surgery", filed Feb. 28, 2001, the disclosure of which is incorporated herein by reference.

BACKGROUND OF THE INVENTION

1. Field of the Invention

The invention generally relates to systems that may be used in performing joint surgery; with a particular embodiment of the invention being described, without limitation, in the context of knee arthroplasty. More particularly, with respect to knee arthroplasty, the invention relates to systems used to properly locate and guide instruments that resect bone in order to achieve a proper cut; and facilitate the proper location and installation of artificial femoral and tibial prosthetic components.

2. Brief Description Of The Prior Art

Total knee arthroplasty involves the replacement of portions of the patellar, femur and tibia with artificial components. In particular, a proximal portion of the tibia and a distal portion of the femur are cut away (resected) and replaced with artificial components.

As used herein, when referring to bones or other body parts, the term "proximal" means closest to the heart and the term "distal" means more distant from the heart. When referring to tools and instruments, the term "proximal" means closest to the practitioner and the term "distal" means distant from the practitioner.

There are several types of knee prostheses known in the art. One type is sometimes referred to as a "resurfacing type". In these prostheses, the articular surface of the distal femur and proximal tibia are "resurfaced" with respective metal and plastic condylar-type articular bearing components.

The femoral component is typically a metallic alloy construction (cobalt-chrome alloy or 6A14V titanium alloy) and provides medial and lateral condylar bearing surfaces of multi-radius design of similar shape and geometry as the natural distal femur or femoral-side of the knee joint.

One important aspect of these procedures is the correct resection of the distal femur and proximal tibia. These resections must provide planes which are correctly angled in order to properly accept the prosthetic components. In particular, the resection planes must be correctly located relative to three parameters: proximal-distal location, varus-valgus angle and flexion-extension angle.

U.S. Pat. No. 5,916,219 (hereby incorporated by reference) discloses an apparatus and method for tibial alignment which allows the independent establishment of two separate geometric planes to be used as a reference for the cutting of the tibial plateau during total knee arthroplasty.

Two separate frame assemblies with telescoping rods are attached to the tibia with a fixed relative angle between them, thereby allowing alignment with the mechanical axis of the bone. A cutting block is mounted on one of the assembly frames and is positioned against the tibia. Stabilizing pins are then placed in the cutting block, allowing the proper tibial plateau resection plane to be created.

The apparatus and method taught in the '219 patent, while solving many prior art problems as indicated therein, has a few disadvantages. The alignment apparatus must be removed prior to performing resection. The device ratchets to discrete locations, preventing a smooth (hereinafter defined as an "infinitely adjustable") alignment. Further, the device can only be used to resect the tibia and cannot be used for femoral resection.

Recently, various computerized systems have been introduced to aid the practitioner during different surgical procedures. A typical, commercially available system is described in the attached Appendix. Such systems typically include multiple video cameras which are deployed above and around the surgical site; and a plurality of dynamic reference frame (DRF) devices, also known as trackers, which are attached to body parts and surgical instruments.

The trackers are generally LED devices which are visible to the cameras. Using software designed for a particular surgical procedure, a computer receiving input from the cameras guides the placement of surgical instruments.

The prior art instruments used for determining the correct planes for tibial and femoral resection in total knee arthroplasty are not well suited for use with computerized systems. The known tools utilize either intra-medullary alignment or extra-medullary alignment techniques and movement in three degrees of freedom is difficult or impossible. Moreover, in order to be useful with computer aided navigation systems, trackers must be attached to the tools. Existing tools do not permit or readily facilitate the attachment of trackers.

Although computer aided navigation systems are superior to unaided visual navigation by the practitioner, computers have known faults. As every computer user knows, any computer can crash or fail in such a way that it may take hours to repair. This is unacceptable during a surgical procedure. Therefore, it is necessary to provide a backup system of some kind so that the procedure may be completed without the failed computer.

SUMMARY OF THE INVENTION

It is therefore an object of the invention to provide methods, systems and tools for performing femoral and tibial resection and indeed, methods, systems and tools similarly useful in performing surgery on other joints (implicit in the objectives and description of the invention set forth herein, although reference to the femur and tibial resection is specifically made for the sake of illustration).

It is also an object of the invention to provide methods, systems and tools for femoral and tibial resection which allow location of a cutting guide relative to three parameters.

It is another object of the invention to provide methods, systems and tools for femoral and tibial resection which are infinitely adjustable.

It is still another object of the invention to provide methods, systems and tools for femoral and tibial resection which are adapted to be used with computer aided navigation systems.

It is also an object of the invention to provide tools which can be used for both femoral and tibial resection.

It is another object of the invention to provide methods, systems and tools for femoral and tibial resection which can be used without computer aided navigation systems should such a system fail during surgery.

In accord with these objects which will be discussed in detail below, the tools of the present invention (again, described in the context of knee surgery for illustrative purposes only), include anchoring devices for attachment to the femur and the tibia, a three-way alignment guide attachable to the anchoring devices and adjustable relative to three parameters, two embodiments of a resection guide attachable to the alignment guide and equipped with couplings for trackers, a plane probe for examining the resected plane, and apparatus for EM alignment of the resection guide in the event of a computer failure.

According to one aspect of the invention, the tibial anchoring device is specially designed to fit the triangular anatomy of the tibia. According to further aspects of the invention, the two resection guides both include rotatable pin guides to allow selection of anchoring pin location; one resection guide may be slotted and according to another embodiment of the invention, one is not slotted.

Further, according to one embodiment of the invention, the apparatus for visual EM alignment includes an EM rod and an EM alignment guide (sometimes referred to as an alignment handle). The EM rod is attachable to the EM alignment guide and the EM alignment guide is attachable to the cutting guide. The EM alignment guide contemplated by a further aspect of the invention has two ends, one of which as adapted for femoral alignment and the other of which is adapted for tibial alignment.

The methods of the invention include operating the computer aided navigation apparatus in the conventional manner including attaching one or more trackers to the bone to be resected; choosing a location for the anchoring device with or without guidance from the computer and installing the anchoring device; attaching the three-way alignment guide to the anchoring device; attaching a resection guide to the alignment guide; attaching one or two trackers to the resection guide; locating the resection guide with the aid of the alignment guide and the computer; fixing the resection guide to the bone with pins through the rotatable pin guides; and resecting the bone.

After the bone is resected, the resection plane probe may be attached to a tracker and moved about the resected plane to obtain feedback from the computer navigation system.

In the event of computer failure, the methods include attaching the EM alignment guide to the resection guide; attaching the EM rod to the EM alignment guide; and locating the resection guide by visual location of the EM rod rather than by feedback from the computer navigation system.

In accordance with the present invention, there is disclosed a system for guiding the resection of a patient's bone during arthroplasty, the system including a resection guide adapted for guiding a cutting device relative to a patient's bone during arthroplasty, an alignment guide coupled to the resection guide and adapted for attachment to the patient's bone, the alignment guide including a first assembly for positioning the resection guide along a translational path, a second assembly for positioning the resection guide along a first rotational path, and a third assembly for positioning the resection guide along a second rotational path, and a computer navigation system coupled to the resection guide.

In accordance with the present invention, there is disclosed a system for guiding the resection of a patient's bone during arthroplasty, the system including a resection guide adapted for guiding a cutting device relative to a patient's bone during arthroplasty, an alignment guide coupled to the resection guide and adapted for attachment to the patient's bone, the alignment guide including a first assembly for positioning the resection guide along a translational path and a second assembly for positioning the resection guide along a first rotational path and a second rotational path, and a computer navigation system coupled to the resection guide.

In accordance with the present invention, there is disclosed a system for guiding the resection of a patient's bone during arthroplasty, the system including a resection guide adapted for guiding a cutting device relative to a patient's bone during arthroplasty, an alignment guide coupled to the resection guide, the alignment guide including a first assembly for positioning the resection guide along a translational path and a second assembly for positioning the resection guide along a first rotational path and along a second rotational path, and a computer navigation system coupled to the resection guide.

In accordance with the present invention, there is disclosed a system for guiding the resection of a patient's bone during arthroplasty, the system including a resection guide adapted for guiding a cutting device relative to a patient's bone during arthroplasty, an alignment guide adapted for positioning the resection guide along a translational path and about a plurality of rotational paths, and a computer navigation system coupled to the resection guide.

BRIEF DESCRIPTION OF THE APPENDIX

The attached ten page Appendix describes the parts and assembly of a computer navigation system suitable for use with the invention. The described parts are commercially available and may be assembled by those skilled in the art according to the assembly instructions, incorporated herein by reference.

DETAILED DESCRIPTION

Turning now to the Figures, the apparatus of the invention will be best understood by a description of the methods of the invention with reference to the Figures.

Figures 1, 2, 3:
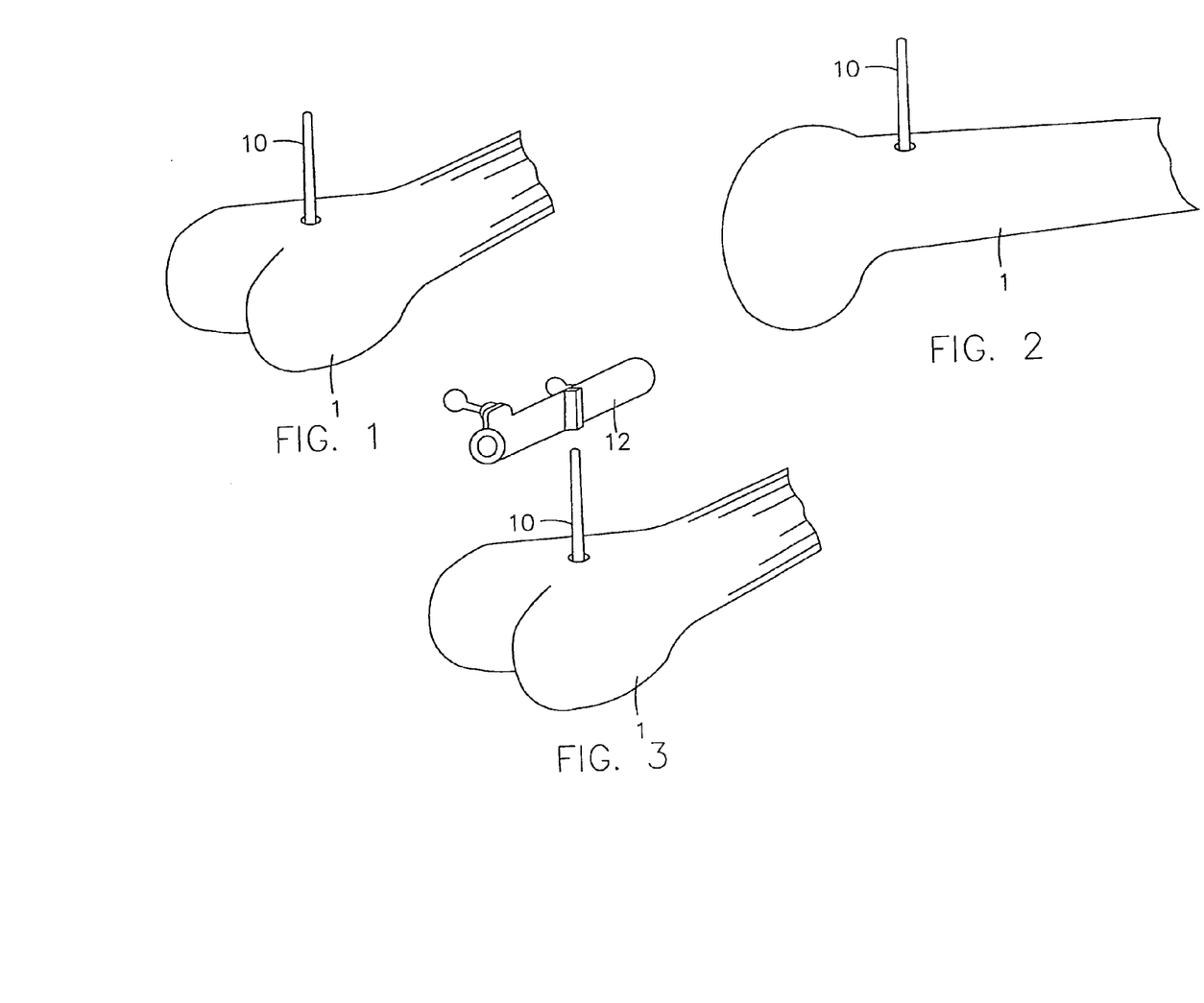
FIG. 1 is a broken perspective view of the distal femur with an anchoring device according to the invention.
FIG. 2 is a side elevational view of the anchoring device installed in the distal femur.
FIG. 3 is a perspective view of the anchoring device installed in the distal femur with a three-way alignment guide according to the invention not yet attached to the anchoring device.

As shown in FIGS. 1 and 2 an anchoring device 10 is installed in the bone 1 in a region proximal to the lateral anterior cortex and within the incision. The location for the anchoring device may be chosen by eye or with the aid of the tracking/navigation software. As shown in the Figures, the anchoring device 10 is a pin which is screwed into the bone. Other anchoring devices such as plates could be used, however.

Figures 4, 5:
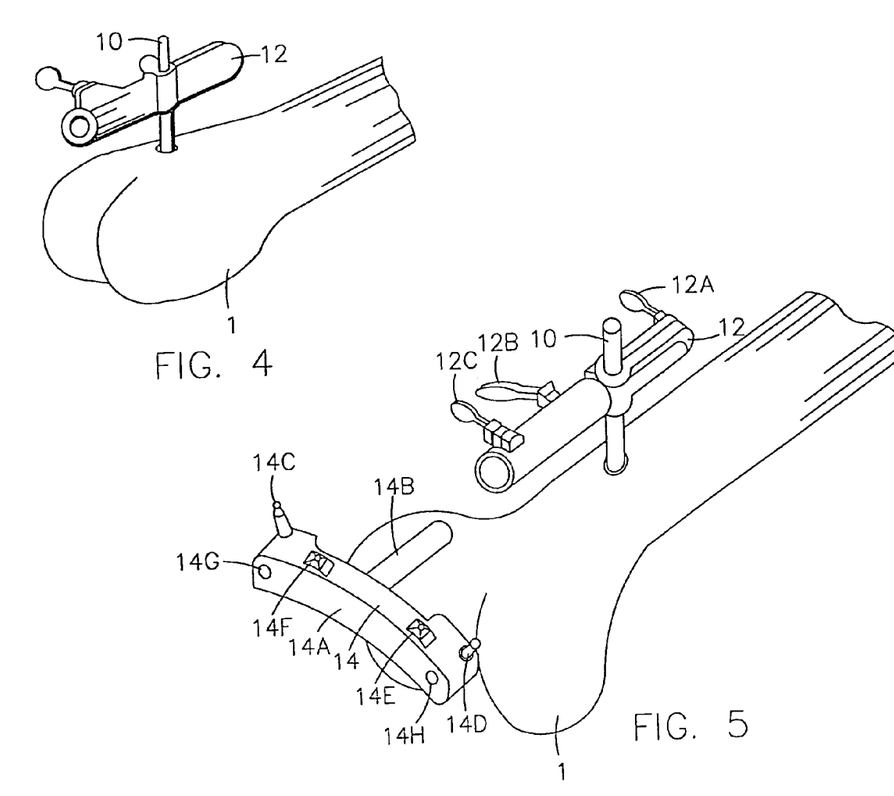
FIG. 4 is a view similar to FIG. 3 showing the alignment guide attached to the anchoring device.
FIG. 5 is a perspective view showing a first embodiment of a resection guide according to the invention not yet attached to the three-way alignment guide.

With the anchoring device 10 in place, the alignment guide 12 is lowered on to it as shown in FIGS. 3-5.

As seen best in FIG. 5, the alignment guide 12 has three cam locks (or equivalent means for releasably locking) 12a, 12b, 12c. The cam lock 12a allows the alignment guide to be adjusted according to varus-valgus angle relative to the anchoring device 10. The cam lock 12b allows the alignment guide to be adjusted according to flexion-extension angle relative to the anchoring device 10. The cam lock 12c opens the end of the alignment device to receive the resection guide 14 shown in FIGS. 5-7.

Figure 6:
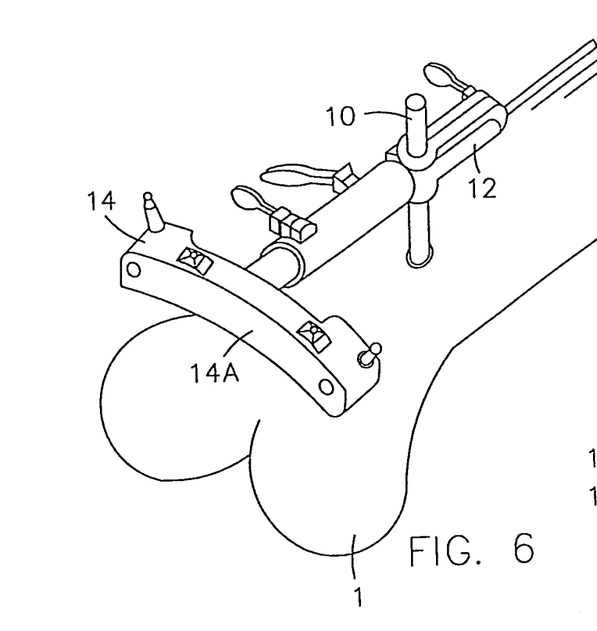
FIG. 6 is a perspective view showing a first embodiment of a resection guide according to the invention attached to the three-way alignment guide.
Figure 7:
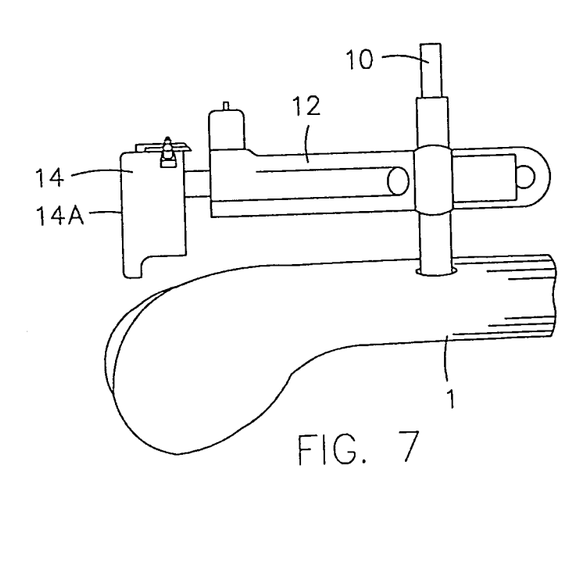
FIG. 7 is a side elevational view showing a first embodiment of a resection guide according to the invention attached to the three-way alignment guide.

Referring now to FIGS. 5-7, the exemplary depicted resection guide 14 has a cutting guide surface 14a, an attachment rod 14b, a pair of connectors 14c, 14d for connecting trackers 100, a pair of rotatable pin guides 14e, 14f, and a pair of fail safe mounting bores 14g, 14h.

The resection guide 14 is attached to the alignment guide 12 by opening cam lock 12c and inserting the attachment rod 14b into the alignment guide. It will be appreciated by those skilled in the art that the cam lock 12c allows proximal-distal positioning of the resection guide 14. After the resection guide 14 is attached to the alignment device 12, a tracker 100 is attached to the guide 14.

With the tracker attached, the first cam lock 12a is opened and the resection guide is moved in the varus-valgus plane until the navigation software indicates the proper alignment. The cam lock 12a is then locked.

Cam lock 12b is unlocked and the resection guide is moved in the flexion-extension plane until the navigation software indicates the proper alignment. The cam lock 12b is then locked. The order of performing the aforementioned steps of unlocking and relocking either or both of cam locks 12a and 12b, may be decided by the surgeon.

Lastly, the cam lock 12c is opened and the resection guide is positioned in the proximal-distal plane until the navigation software indicates the proper alignment. The cam lock 12c is then locked. With the resection guide properly located, it may be affixed to the bone with pins (not shown) via the rotatable pin guides 14e, 14f. The pin guides are rotatable so that the practitioner may choose the best site for inserting a pin. The next step in the procedure is to resect the distal end of the femur using the resection guide 14.

Those skilled in the art will appreciate that if the anchor pin 10 is not substantially perpendicular to the varus-valgus plane, the steps may need to be repeated to tune out error introduced by the misaligned anchor pin. One possible solution is to install the pin with a drill having an attached tracker thereby allowing the navigation software to guide the placement of the pin.

Figure 8:
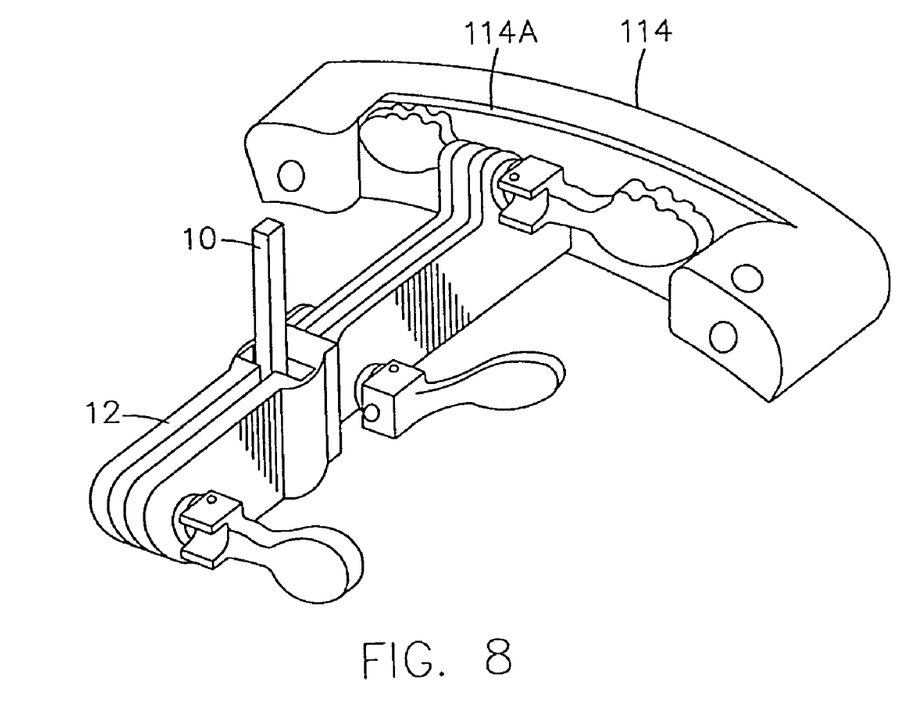
FIG. 8 is a perspective view showing a second embodiment of a resection guide according to the invention attached to the three-way alignment guide.

FIG. 8 illustrates an alternate embodiment of a resection guide 114. The resection guide 114 is identical to the resection guide 14 except that it has a slot 114a for the cutting tool (not shown). Some practitioners prefer slotted cutting guides and others prefer non-slotted guides.

Figure 9:
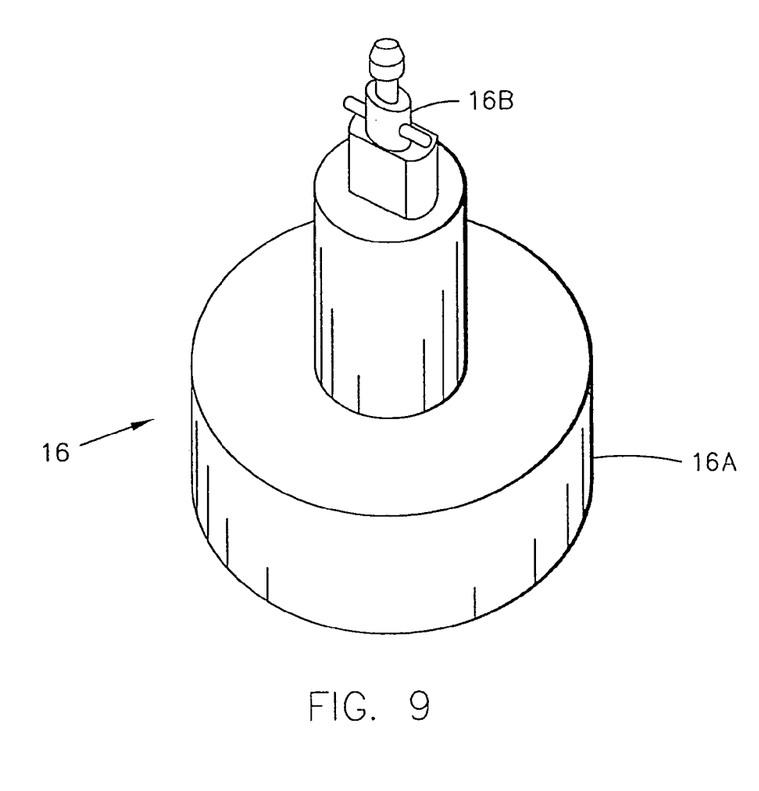
FIG. 9 is a perspective view of a resection plane probe according to the invention.

After the distal femur is resected, the accuracy of the cut can be checked using the resection plane probe 16 shown in FIG. 9. The probe 16 has a smooth planar surface 16a and a coupling 16b for attaching a tracker. With a tracker attached to the probe, it is moved about the resected surface and the navigation software determines the accuracy of the resection.

Figure 10:
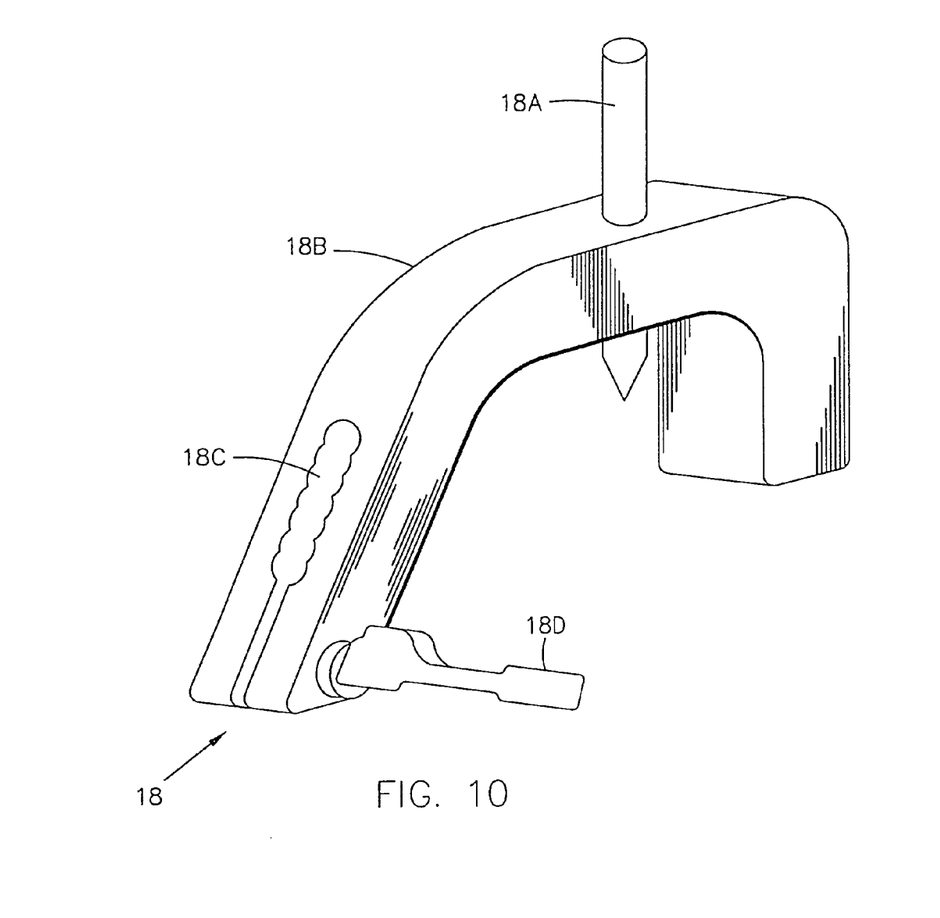
FIG. 10 is a perspective view of a tibial anchoring device according to the invention.

All of the procedures described above can now be repeated to resect the proximal end of the tibia. Due to the triangular shape of the tibia, a special anchoring device 18, shown in FIG. 10, is used.

The anchoring device 18 has an anchoring post 18a for attaching the alignment guide, an angled body 18b, a side slot 18c, and a slot clamp 18d. The anchoring device 18 is attached to the tibia by inserting a pin through the slot 18c into the medial side of the tibia in a region within the incision and distal to the tibial tubercle. The clamp 18d is closed to clamp the slot 18c relative to the pin (not shown).

It will be appreciated by those skilled in the art that the slot 18c has a plurality of grooves to snugly grab the pin. With the anchoring device 18 in place, the procedure described above is repeated to resect the proximal tibia.

Although the computerized navigation systems are a major advance in arthroplasty, computers often fail and at most inopportune times. The present invention provides a fail safe back up system for use when a computerized navigation system fails.

Figures 11, 12:
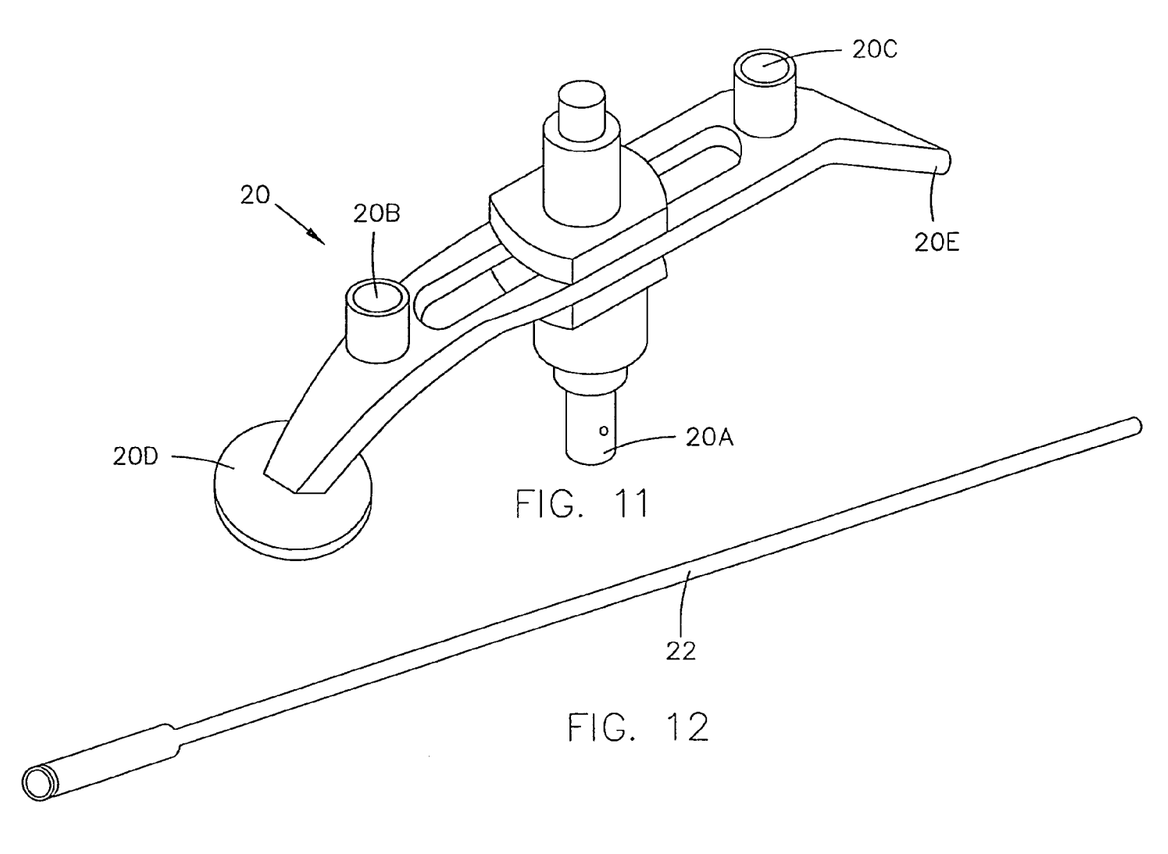
FIG. 11 is a perspective view of a fail safe EM alignment guide according to the invention.
FIG. 12 is a perspective view of an extra medullary alignment rod for use with the EM alignment guide shown in FIG. 11.
Figure 13:
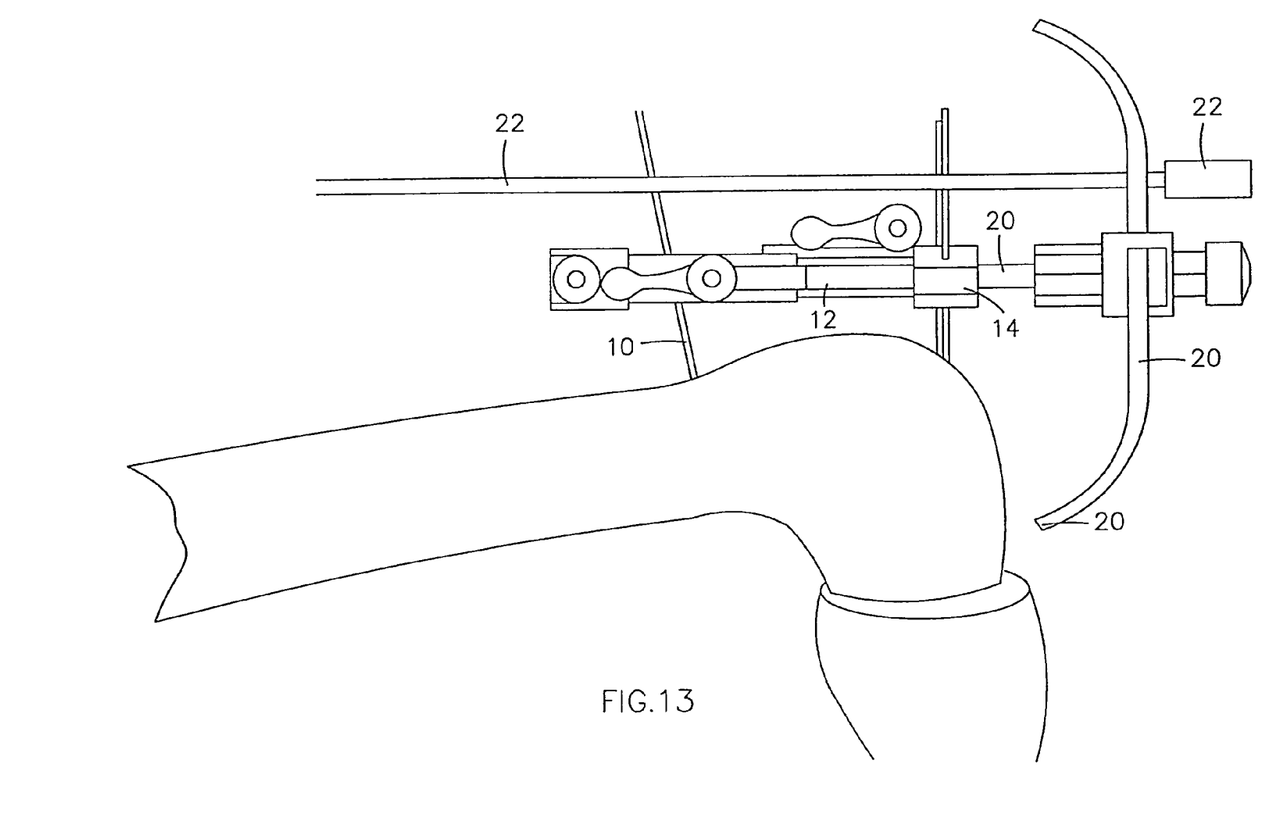
FIG. 13 is a side elevational view of the fail safe EM alignment guide attached to the resection cutting guide with the EM rod attached to the EM alignment guide.

Referring now to FIGS. 11-13, the invention provides a manual EM alignment guide 20 and an EM alignment rod 22. The guide 20 includes a mounting shaft 20a, two bores 20b, 20c for receiving the EM rod, a femur guide 20d and a tibia guide 20e.

The mounting shaft 20a is inserted into one of the fail safe bores (14g, 14h in FIG. 5) of the resection guide 14 and the EM rod 22 is inserted into one of the bores 20b, 20c in the guide 20. When used with the femur, the EM rod 22 is inserted through the bore 20c and the femur guide 20d is placed against the distal end of the femur as shown in FIG. 13. Flexion-extension and varus-valgus positioning may then be accomplished visually using the EM rod. For use with the tibia, the EM rod is placed on the other bore and the tibia guide is placed against the proximal tibia.

There have been described and illustrated herein methods and tools for resection of the distal femur and proximal tibia. While particular embodiments of the invention have been described, it is not intended that the invention be limited thereto, as it is intended that the invention be as broad in scope as the art will allow and that the specification be read likewise. For example, as indicated hereinbefore, the first two positioning steps may be reversed in sequence, provided that the navigation software is suitably modified. Moreover, the clamps on the alignment guide need not be cam locks, but could be other types of clamps.

Although the apparatus has been described as three separate pieces (the anchor, the alignment guide, and the resection guide), it could be two pieces or a single piece. If it were a single piece, it will be appreciated that separate devices would preferably be provided for tibia and femur.

In general, as previously indicated, the methods and tools of the invention could be used with other joints other than the knee. It is believed that the methods and tools could be used in arthroplasty of the hip, shoulder, elbow, etc.

It will therefore be appreciated by those skilled in the art that yet other modifications could be made to the provided invention without deviating from its spirit and scope as so claimed.

What is claimed is:

1. A system for guiding the resection of a patient's bone during arthroplasty, said system comprising a resection guide adapted for guiding a cutting device relative to a patient's bone during arthroplasty, an alignment guide coupled to said resection guide and adapted for attachment to the patient's bone, said alignment guide including a first assembly for positioning said resection guide along a translational path, a second assembly for positioning said resection guide along a first rotational path, and a third assembly for positioning said resection guide along a second rotational path, and a computer navigation system coupled to said resection guide, the system further including an anchoring pin adapted to secure said alignment guide to a patient's bone.

2. A system of claim 1, wherein said first and second rotational paths are about different axes.

3. A system of claim 2, wherein said axes are transverse to each other.

4. A system of claim 1, wherein said first, second and third assemblies each include a locking device for securing said resection guide along said translational path and said first and second rotational paths.

5. A system of claim 1, further including a computer navigation tracker coupled to said resection guide.

6. A system of claim 1, further comprising a plane probe, said plane probe including a planar surface and coupling means for coupling said plane probe to a computer navigation tracker.

7. A system for guiding the resection of a patient's bone during arthroplasty, said system comprising a resection guide adapted for guiding a cutting device relative to a patient's bone during arthroplasty, an alignment guide coupled to said resection guide and adapted for attachment to the patient's bone, said alignment guide including a first assembly for positioning said resection guide along a translational path and a second assembly for positioning said resection guide along a first rotational path and a second rotational path, and a computer navigation system coupled to said resection guide, the system further including an anchoring pin adapted to secure said alignment guide to a patient's bone.

8. A system of claim 7, wherein said first and second rotational paths are about different axes.

9. A system of claim 8, wherein said axes are transverse to each other.

10. A system of claim 7, wherein said first and second assemblies each include a locking device for securing said resection guide along said translational path and said first and second rotational paths.

11. A system of claim 7, further including a computer navigation tracker coupled to said resection guide.

12. A system according to claim 7, further comprising a plane probe, said plane probe including a planar surface and coupling means for coupling said plane probe to a computer navigation tracker.

13. A system for guiding the resection of a patient's bone during arthroplasty, said system comprising a resection guide adapted for guiding a cutting device relative to a patient's bone during arthroplasty, an alignment guide coupled to said resection guide and adapted for attachment to the patient's bone, said alignment guide including a first assembly for positioning said resection guide along a translational path and a second assembly for positioning said resection guide along a first rotational path and along a second rotational path, and a computer navigation system coupled to said resection guide, the system further including an anchoring pin adapted to secure said alignment guide to a patient's bone.

14. A system of claim 13, wherein said first and second rotational paths are about different axes.

15. A system of claim 14, wherein said axes are transverse to each other.

16. A system of claim 13, wherein said first and second assemblies each include a locking device for securing said resection guide along said translational path and said first and second rotational paths.

17. A system of claim 13, further including a computer navigation tracker coupled to said resection guide.

18. A system according to claim 13, further comprising a plane probe, said plane probe including a planar surface and coupling means for coupling said plane probe to a computer navigation tracker.

19. A system according to claim 18, further comprising a plane probe, said plane probe including a planar surface and coupling means for coupling said plane probe to a computer navigation tracker.

20. A system for guiding the resection of a patient's bone during arthroplasty, said system comprising a resection guide adapted for guiding a cutting device relative to a patient's bone during arthroplasty, an alignment guide adapted for attachment to the patient's bone and adapted for positioning said resection guide along a translational path and along a plurality of rotational paths, and a computer navigation system coupled to said resection guide, the system further including an anchoring pin adapted to secure said alignment guide to a patient's bone.

21. A system of claim 20, wherein said plurality of rotational paths are about different axes.

22. A system of claim 21, wherein said axes are transverse to each other.

23. A system of claim 20, wherein said alignment guide includes first and second assemblies each including at least one locking device.

24. A system of claim 23, wherein said locking device of said first assembly is adapted for securing said resection guide along said translational path.

25. A system of claim 23, wherein said locking device of said second assembly is adapted for securing said resection guide along said plurality of rotational paths.

26. A system of claim 25, wherein said second assembly includes a pair of locking devices, each of said locking devices adapted for securing said resection guide along separate rotational paths.

27. A system of claim 20, further including a plane probe.

* * * * *